United States Patent [19]
Fitzpatrick

[11] Patent Number: 4,926,681
[45] Date of Patent: May 22, 1990

[54] CONTAINER CONTENT TESTER

[75] Inventor: Nicholas B. Fitzpatrick, Haslemere, England

[73] Assignee: The BOC Group plc, Windlesham, England

[21] Appl. No.: 242,017

[22] Filed: Sep. 8, 1988

[30] Foreign Application Priority Data

Sep. 9, 1987 [GB] United Kingdom ............... 8721175

[51] Int. Cl.⁵ .................. G01D 21/02; G01N 7/00; G01N 27/28
[52] U.S. Cl. ............................. 73/52; 73/19
[58] Field of Search ............ 73/52, 19, 61 R, 37, 73/714; 204/431, 432, 14, 18, 15

[56] References Cited

U.S. PATENT DOCUMENTS

| | | | |
|---|---|---|---|
| 3,849,070 | 11/1974 | Garza et al. | 23/230 R |
| 3,958,448 | 5/1976 | Willis et al. | 73/52 X |
| 4,089,208 | 5/1978 | Franks et al. | 73/49.3 X |
| 4,133,736 | 1/1979 | Nakagawa et al. | 204/195 P |
| 4,152,213 | 5/1979 | Ahnell | 435/34 |
| 4,208,903 | 6/1980 | Hopper et al. | 73/52 |
| 4,281,536 | 8/1981 | Kraft et al. | 73/52 X |
| 4,282,182 | 8/1981 | Webster | 73/864.23 X |
| 4,555,935 | 12/1985 | Elert | 73/52 |
| 4,733,555 | 3/1988 | Franks | 73/52 X |

Primary Examiner—Tom Noland
Attorney, Agent, or Firm—David A. Draegert; Larry R. Cassett

[57] ABSTRACT

Apparatus for testing the contents of a sealed container 10 holding a liquid under the pressure of gas in a head space includes a first piercing needle 18 positioned and operable to penetrate the top of the container 10 whereby to place the head space in communication with a gas passage way 20 and a second piercing needle 56 positioned and operable to penetrate the bottom of the container 10 whereby to place the liquid in communication with a liquid passage way 58. The apparatus may be used to measure the gas pressure in the container and the dissolved oxygen content of the liquid.

12 Claims, 3 Drawing Sheets

CONTAINER CONTENT TESTER

BACKGROUND OF THE INVENTION

The present invention relates to an apparatus and method for testing the contents of a sealed container holding a liquid under the pressure of gas in a headspace. The container is typically a can and the liquid may for example be a beverage in which gas is dissolved.

It is the practice in the soft drinks industry to test the contents of a small proportion of cans filled with typically a carbonated beverage during a production run. One of the tests made is to measure the pressure in the headspace of the can to indicate the carbonation of the beverage. Another test is to measure the dissolved oxygen concentration of the beverage. It is necessary for the dissolved oxygen concentration of the beverage to be below a given maximum as oxygen may react with substances in the beverage to cause deterioration of the beverage.

Conventionally, the two tests mentioned above are conducted separately. The can is pierced with a hollow needle having a relatively wide bore. The needle communicates with the pressure gauge. An inner steel tube is inserted through the needle into the liquid in the can and acts as a siphon for withdrawing a sample of the liquid for a measurement of its dissolved oxygen concentration. This arrangement has a disadvantage in that the needle and its associated tubes add appreciably to the volume of the headspace of the can and thus causes inaccuracy in the measurement of the pressure in the headspace.

It is an aim of the invention to provide a method and apparatus that makes it possible to mitigate this problem.

SUMMARY OF THE INVENTION

According to the present invention there is provided an apparatus for testing the contents of a sealed container holding a liquid under the pressure of gas in a headspace, including a first piercer positioned and operable to penetrate the top of the container whereby to place the headspace of the container in communication with at least one gas passageway, and a second piercer positioned and operable to penetrate the bottom of the container whereby to place the liquid in communication with the liquid passageway.

The invention also provides a method for testing the contents of a sealed container holding a liquid under the pressure of gas in a headspace, including piercing the top of the container and passing gas from the headspace through a gas passageway for testing, and then piercing the bottom of the container and passing a liquid from the container through a liquid passageway for testing.

The terms 'top' and 'bottom' are relative to the position of the container in the apparatus and method according to the invention.

The invention makes it possible to employ passageways having very small volumes, typically, each under one cubic centimeter, thus making possible relatively accurate measurement of the pressure in the headspace and of the concentration of the chosen dissolved gas, typically oxygen, in the liquid.

In addition the invention allows for the pre-setting of an accurate counter pressure prior to discharge of the can contents, reducing gas breakout and further improving the accuracy of dissolved gas measurement.

Preferably, said at least one gas passageway extends through a body member, and the first piercer comprises a hollow needle having its proximal end mounted in the body and communicating with said gas passageway. Typically, the gas passageway terminates at one end in one face of the body member and at its other end at an opposite face of the body member. Preferably, a gas passageway at one end receives a pressure gauge and at its other end a pipe having a valve disposed therein enabled to be placed in communication with a source of gas under pressure. This arrangement enables a counter pressure to be applied to the headspace once the gas pressure has been measured therein, which counter pressure can be maintained during the withdrawal of liquid from the bottom of the container so as to reduce the amount of the chosen dissolved gas that comes out of solution during this procedure.

BRIEF DESCRIPTION OF THE DRAWINGS

The apparatus and method according to the present invention will now be described by way of example with reference to the accompanying drawings, in which.

DETAILED DESCRIPTION OF THE INVENTION

Figure 1:
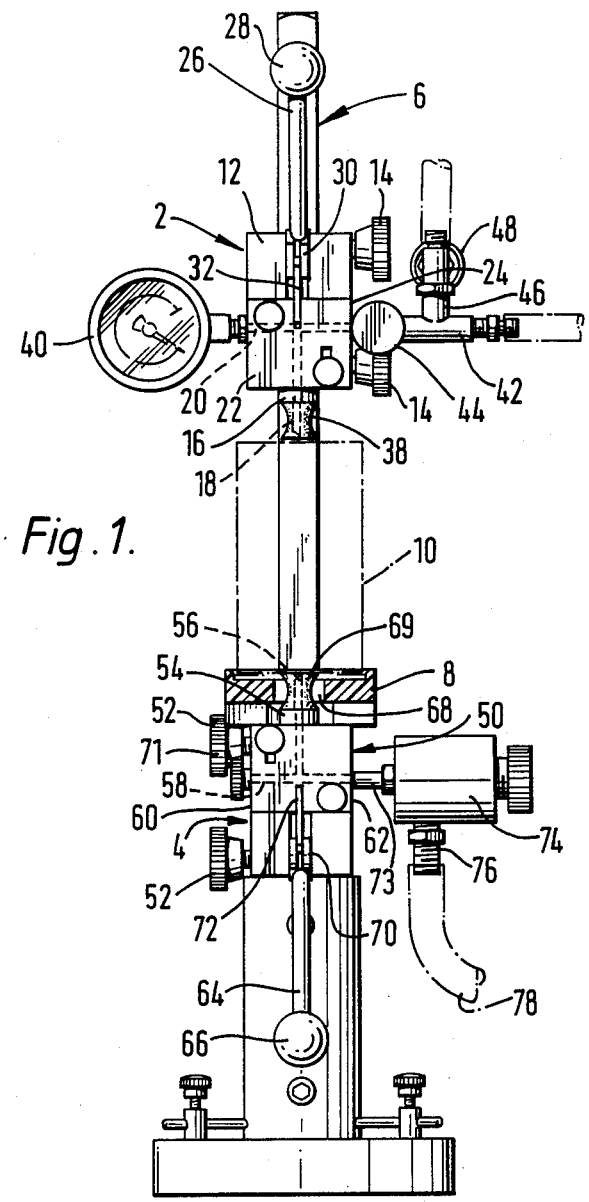
FIG. 1 is a front elevation, partly in section, of a can testing apparatus according to the invention.

Referring to the drawings, the can testing apparatus includes an upper can piercing assembly 2 and a lower can piercing assembly 4. The assemblies 2 and 4 are mounted on a stand 6. The stand 6 also carries a platform 8 on which a can 10 (or other such container), shown in dashed lines in the drawings, is supported. The upper piercing assembly 2 comprises a block 12 which may be slid up and down the stand and secured in a chosen can piercing position by operation of bolts 14. The block 12 guides a body member 16 for vertical movement. The body member 16 carries a vertical hollow needle 18 whose proximal end communicates with a gas passageway 20 extending through the body member 16 from one side face 22 to an opposite side face 24 thereof.

Figure 2:
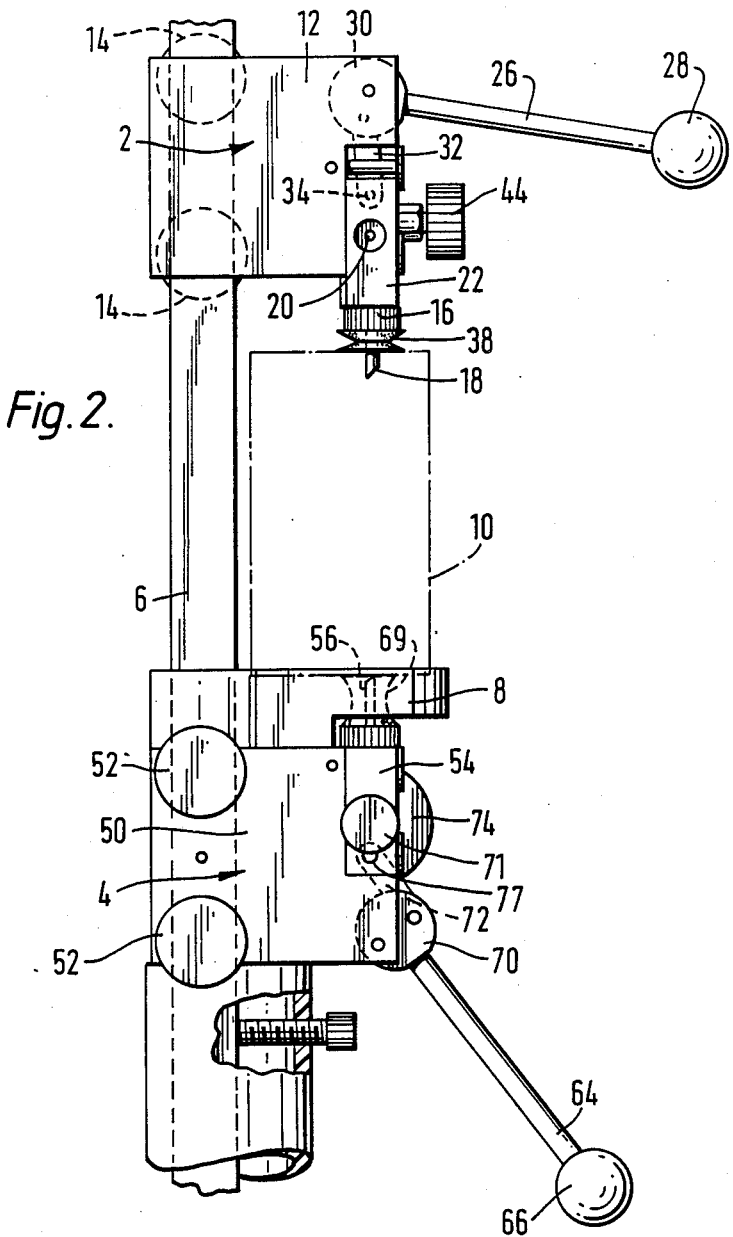
FIG. 2 is a side view of the apparatus shown in FIG. 1, in which the top of a can is shown pierced.
Figure 3:
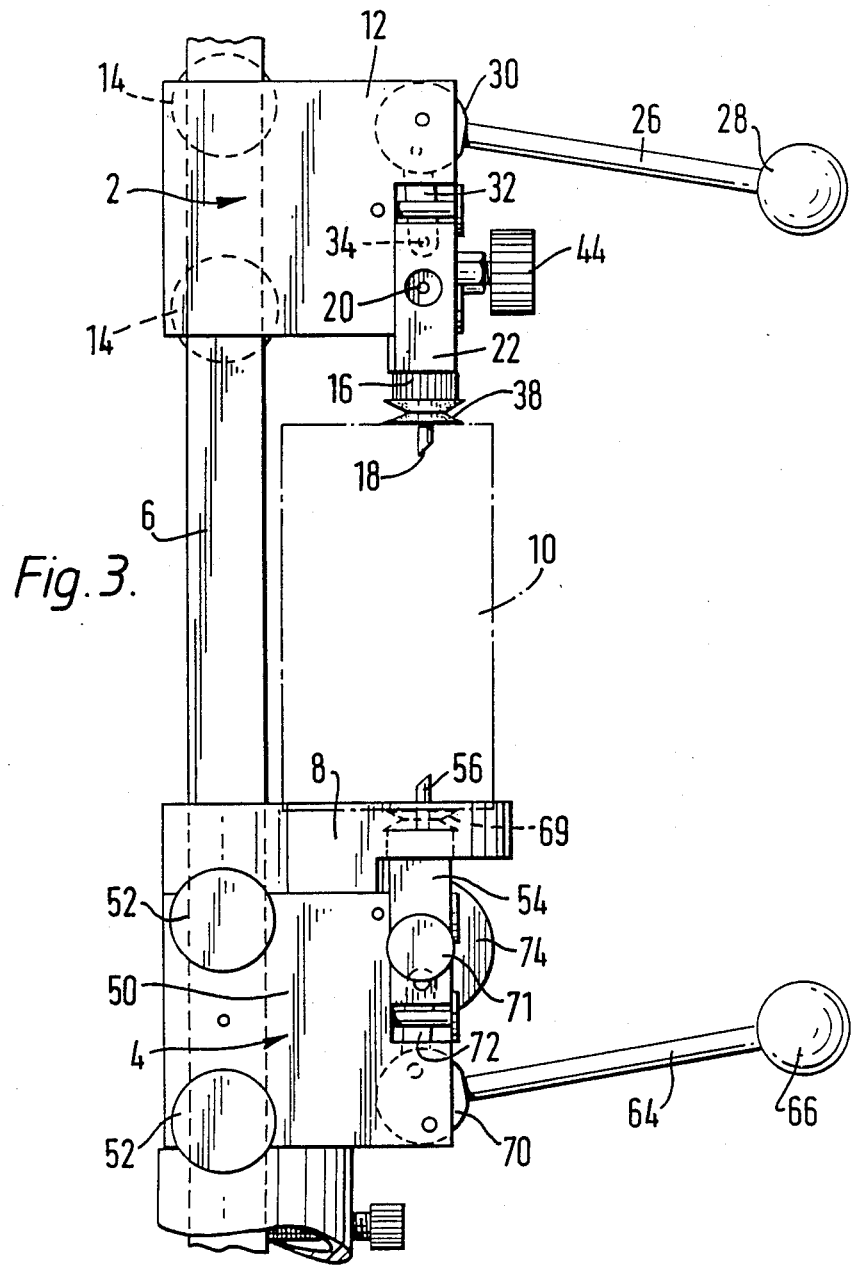
FIG. 3 is a view similar to that of FIG. 2 but showing both the top and bottom of the can pierced.

The needle 18 may be lowered so as to pierce the can 10 by lowering (from the position shown in FIG. 1 to the position shown in FIGS. 2 and 3) an arm 26 having an a handle 28 at one end and at its other end being received in a shaft 30 which, as shown in FIGS. 2 and 3 has eccentrically connected thereto a link 32. The link 32 is also connected by a pin 34 to the body member 16. The arrangement is such that downward displacement of the arm 26 moves downwards the point of connection between the link 32 and the shaft 30 such that there is a corresponding downward movement of the body member 16. The needle 18 is formed of steel sufficiently strong to penetrate the top of the can without itself being distorted. As the arm 26 is lowered so an elastomeric bush 38 engaged between the top of the can 10 and the body member 16 is compressed to make a gas-tight seal as the needle 18 penetrates the top of the can 10.

The end of the passageway 20 terminating in the face 22 receives a pressure gauge 40 whereby pressure in the headspace can be measured. In FIGS. 2 and 3, the pressure gauge, for purposes of clarity of illustration, is not shown. The end of the passageway 20 terminating in the face 24 of the block 12 receives a pipe 42 having a manually operable stop valve 44 located therein at a region near this end. The opposite end of the pipe 42 may be connected to a cylinder of gas such as nitrogen (not shown). A vent pipe 46 terminates in the pipe 42 at a region intermediate the ends of the pipe 42. The vent pipe 46 has a manually operable valve 48 disposed therein. In use, if it is desired to smell the gas in the headspace of the can 10 the valves 44 and 48 may be opened to vent the gas from the headspace.

The lower piercer assembly 4 is substantially the same as the upper piercer assembly 2 save that it is disposed such that an upward movement rather than a downward movement of the needle causes the bottom of the can to be pierced. The piercer assembly 4 includes a block 50 which is able to be slid up and down the stand and can be secured in a chosen position by tightening bolts 52. The block 50 guides a body member 54 for vertical movement. The body member 54 has the proximal end of a hollow vertically disposed needle 56 disposed therein. The proxmial end of the needle 56 communicates with a passageway 58 extending laterally through the body member 54 from one side face 60 to an opposite side face 62 of the body member 54.

Upward movement of the needle 56 is effected by raising an arm 64 (having a handle 66) from the position shown in FIGS. 1 and 2 to the position shown in FIG. 3. The needle 56 extends through a passage 68 in the platform 8 on which the can 10 is seated. Raising the arm 64 causes a shaft 70 in which the arm 64 is received to rotate. The shaft 70 is eccentrically connected by link 72 to a pin 77 carried by the body member 54. The rotation of the shaft 70 caused by raising the arm 64 urges the link 72 upwards and thus moves the needle 56 upwards. The needle 56 is made of a steel sufficiently strong to enable it to pierce the bottom of the can 10 without itself being deformed. As the arm 64 is raised so an elastomeric bush 69 engaged between the bottom of the can 10 and the body member 54 is compressed to make a seal as the needle 56 pierces the can. The end of the passageway 58 that terminates in the face 60 of the block 50 is closed by a manually operable valve 71. The other end of the passageway 58 receives the inlet 73 to an electrochemical cell 74, typically of the Clarke type, for measuring dissolved oxygen concentration. The cell 74 may form part of a commercial dissolved oxygen meter. The cell 74 has an outlet 76 connected by tubing 78 to a drain so that after passing over the face of the cell membrane (not shown) the liquid from the can 10 may be drained away.

The piercing assemblies 2 and 4 are advantageously assemblies of a kind previously employed for measuring gas pressure. For example, they may be Reeve carbonation testers. Thus, the apparatus shown in the drawings may be made from standard components save for the platform 8 which can readily be formed as a plastics moulding.

In operation, the piercing assemblies 2 and 4 are suitably positioned on the stand 6. A can 10 is placed on the platform 8. The top of the can 10 is then pierced by lowering the arm 26 to cause the needle 18 to penetrate the top of the can 10 and thus assume the position shown in FIG. 2 of the drawings. The pressure gauge 40 is thus placed in communication with the headspace of the can and so the pressure in the headspace can be measured. Valve 44 is then opened, but valve 48 is kept closed, to permit a gas pressure preferably the same or a little above that recorded by the pressure gauge 40 to be applied to the headspace. The arm 64 is then raised to the position shown in FIG. 3 cause the needle 56 to penetrate the bottom of the can 10. Liquid is thus caused to flow through the passageway 58 into the cell 74 to enable its dissolved oxygen concentration to be measured using the dissolved oxygen meter (which may for example be of the kind made by Jenway Ltd of Felsted, Essex).

If it is desired to smell the contents of the headspace, then, prior to piercing the bottom of the can the valve 48 may be momentarily opened.

The passageways 20 and 58 are typically of very small volume, for example less than 1 cubic centimeter each, to permit relatively accurate measurements of the gas pressure and dissolved oxygen concentration to be made.

If desired, an apparatus according to the invention may be operated with the can supported at an angle of 90° to that shown in the drawings but with the piecers still vertically displaceable.

I claim:

1. Apparatus for testing the contents of a sealed container holding a liquid under the pressure of gas in a head space, including a first piercer positioned and operable to penetrate a top of the container whereby to place the headspace of the container in communication with at least one gas passageway, and a second piercer positioned and operable to penetrate a bottom of the container whereby to place the liquid in communication with a liquid passageway.

2. Apparatus according to claim 1, in which said at least one gas passageway extends through a body member, and the first piercer comprises a hollow needle having its proximal end mounted in the body and communicating with said gas passageway.

3. Apparatus according to claim 2, in which said gas passageway terminates at one end in one face of the body member and at its other end in an opposite face of the body member.

4. Apparatus according to claim 1, in which the gas passageway at one end receives a pressure gauge and at its other end a pipe having a valve disposed therein and able to be placed in communication with a source of gas under pressure.

5. Apparatus according to claim 1, in which said liquid passageway extends through a body member, and the second piercer comprises a hollow needle having its proximal end mounted in the body and communicating with said liquid passageway.

6. Apparatus according to claim 1, in which the liquid passageway communicates with an electrochemical cell forming part of a dissolved oxygen meter.

7. Apparatus according to claim 1, additionally including a platform on which said container is able to be seated, the platform having a passage therethrough to permit the second piercer to be urged into a position in which it penetrates the bottom of the container.

8. Apparatus according to claim 1, in which said gas and liquid passageways each have a capacity of less than one cubic centimeter.

9. A method for testing the contents of a sealed container holding a liquid under the pressure of gas in a headspace, including piercing a top of the container and passing gas from the headspace through a gas passageway for testing, and then piercing a bottom of the container and passing a liquid from the container through a liquid passageway for testing.

10. A method according to claim 9, in which between piercing the top of the container and the bottom of the container the gas pressure in the headspace is measured and a counter-pressure of gas is applied to the headspace.

11. A method according to claim 10, in which after the bottom of the container is pierced liquid is withdrawn from the liquid passageway and its dissolved oxygen concentration is measured.

12. A method according to claim 9, in which the container is a can.

* * * * *